(12) United States Patent
Smith

(10) Patent No.: US 7,255,251 B1
(45) Date of Patent: Aug. 14, 2007

(54) HOLDING APPLIANCE FOR FACILITATING BLOOD DRAWING PROCESS

(76) Inventor: Jason Smith, 3023 N. Clark St. PMB 295, Chicago, IL (US) 60657

( * ) Notice: Subject to any disclaimer, the term of this patent is extended or adjusted under 35 U.S.C. 154(b) by 644 days.

(21) Appl. No.: 10/208,928

(22) Filed: Jul. 31, 2002

Related U.S. Application Data

(60) Provisional application No. 60/308,899, filed on Jul. 31, 2001.

(51) Int. Cl.
*A44C 5/18* (2006.01)
(52) U.S. Cl. ............... 224/221; 604/179; 604/231
(58) Field of Classification Search ........ 224/218–222; 604/231, 179
See application file for complete search history.

(56) References Cited

U.S. PATENT DOCUMENTS

| | | | | |
|---|---|---|---|---|
| D257,240 S | * | 10/1980 | Leary | D10/114 |
| 4,712,766 A | * | 12/1987 | Ehrenhalt | 251/90 |
| D302,075 S | * | 7/1989 | Burger | D3/218 |
| 5,009,347 A | * | 4/1991 | Phelps | 224/219 |
| D328,820 S | * | 8/1992 | Davie | D3/229 |
| 5,147,329 A | * | 9/1992 | Brannon | 604/231 |
| 5,154,506 A | * | 10/1992 | Leard | 362/103 |
| 5,259,392 A | * | 11/1993 | Schmitt | 600/576 |
| 5,496,282 A | * | 3/1996 | Militzer et al. | 604/179 |
| D375,624 S | * | 11/1996 | Jensen | D3/229 |
| 5,752,633 A | * | 5/1998 | Antaki | 224/222 |
| 5,855,307 A | * | 1/1999 | Biddick et al. | 224/267 |
| 5,897,519 A | * | 4/1999 | Shesol et al. | 602/79 |
| 6,086,564 A | * | 7/2000 | McLaughlin | 604/179 |
| 6,113,577 A | * | 9/2000 | Hakky et al. | 604/174 |
| 6,461,319 B1 | * | 10/2002 | Ekey | 602/62 |

* cited by examiner

*Primary Examiner*—Stephen K. Cronin
(74) *Attorney, Agent, or Firm*—Drinker Biddle & Reath LLP

(57) ABSTRACT

An appliance for facilitating the blood drawing process comprising a band to be worn across the wrist of the phlebotomist intending to draw the blood, the wrist band including a holder for retaining a blood collection barrel in place on the phlebotomist's wrist and in clear view while both of the phlebotomist's hands are free to perform the blood drawing process.

16 Claims, 2 Drawing Sheets

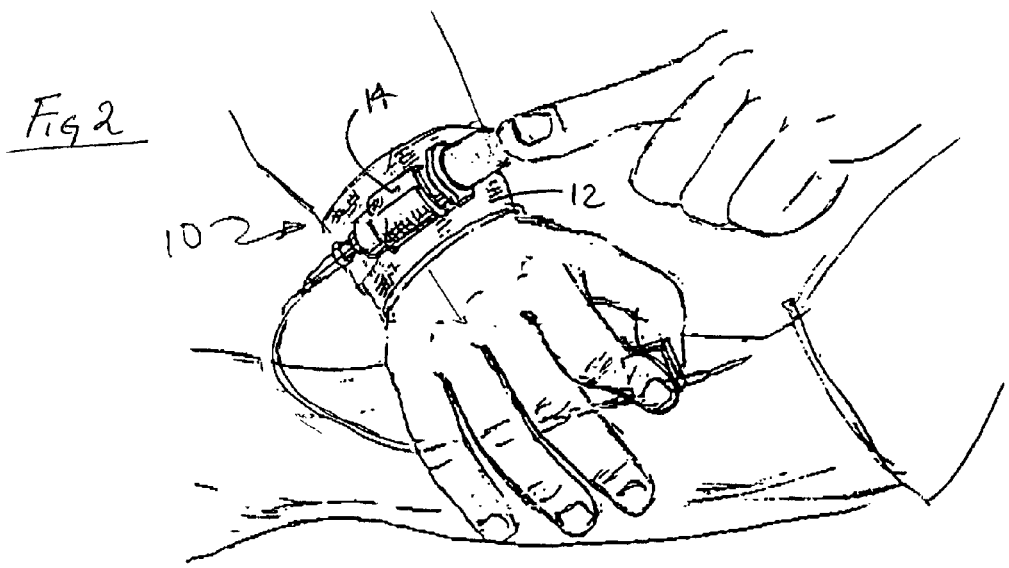
Fig 2
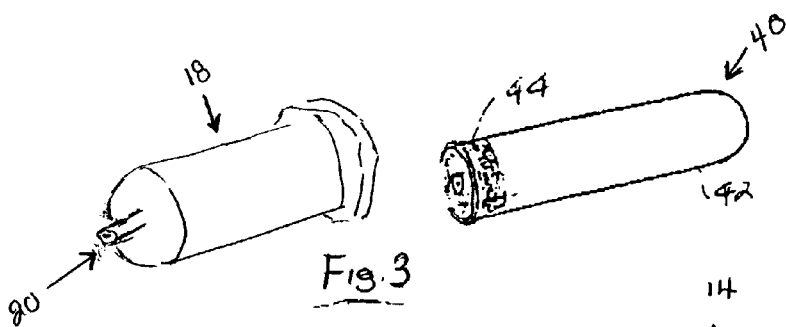
Fig. 3
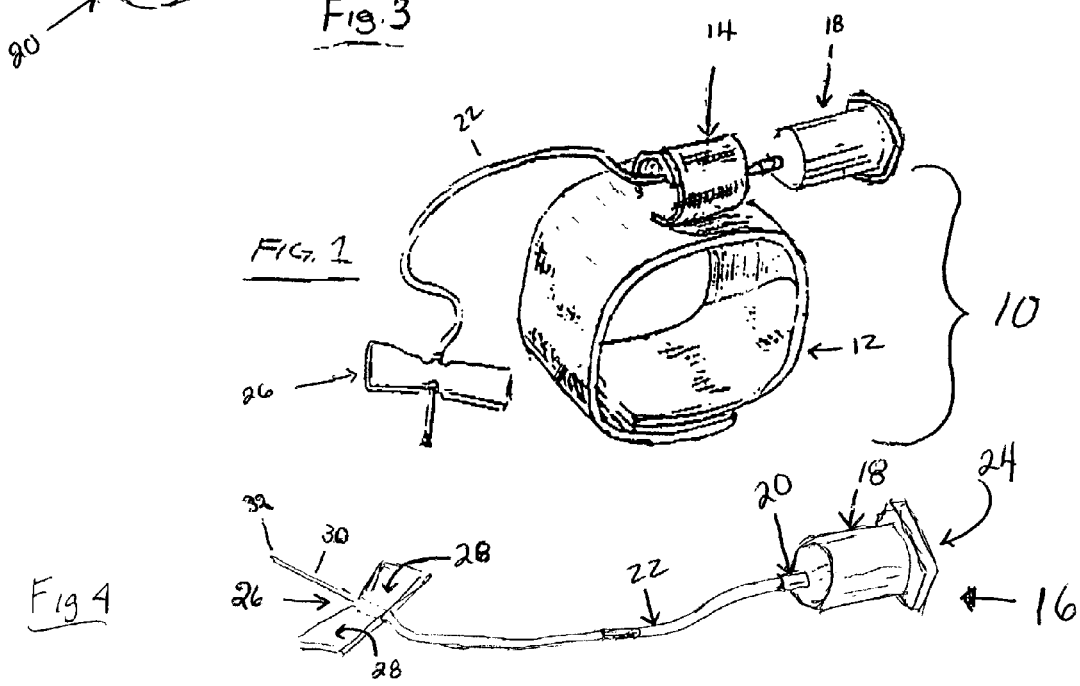
Fig. 1
Fig 4

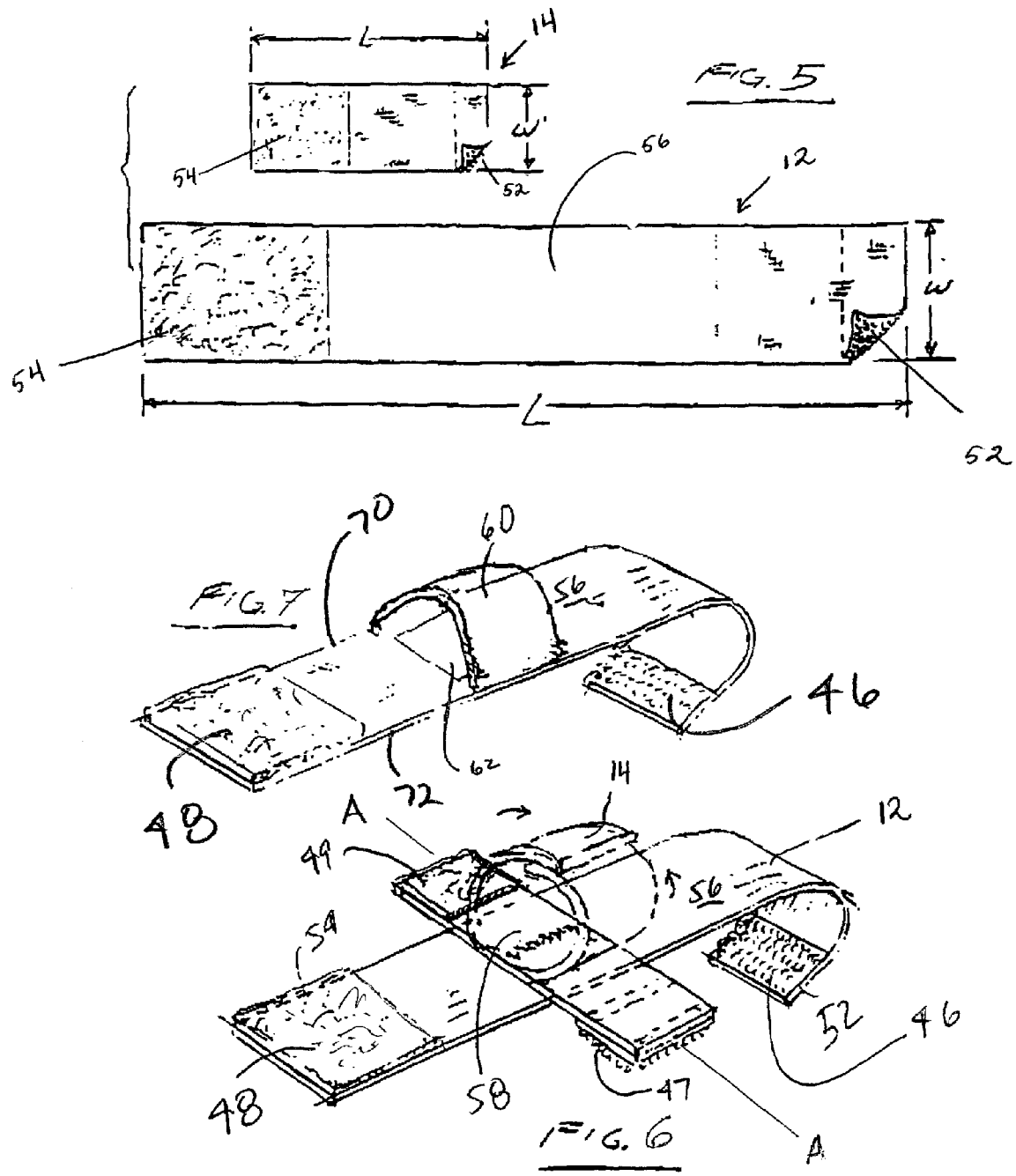

HOLDING APPLIANCE FOR FACILITATING BLOOD DRAWING PROCESS

This application claims priority of U.S. Provisional Patent Application 60/308,899, filed Jul. 31, 2001.

BACKGROUND OF THE INVENTION

This invention relates generally to an appliance for facilitating the blood drawing process. More particularly, this invention relates to an appliance uniquely adapted for use in drawing blood from children or adults. In one especially important embodiment, the appliance is used with a conventional vacuum blood collection container system and a conventional blood draw cannula assembly such as a "butterfly" blood drawing assembly.

SUMMARY OF THE INVENTION

The invention generally comprises an appliance for facilitating the blood drawing process. It includes a band designed to be worn across the wrist of the phlebotomist intending to draw the blood. The wrist band includes a holder for removably retaining a blood collection container barrel on the drawer's wrist, leaving both of the drawer's hands free to perform the conventional steps of the blood drawing process.

BRIEF DESCRIPTION OF THE DRAWINGS

These and other features, aspects, and advantages of the present invention will be better understood from the following description, appended claims, and accompanying drawings where:

FIG. 1 is a perspective view of a holding appliance of the invention, as well as the attached butterfly needle and blood collection barrel in which the blood collection barrel is about to be inserted into the holder of the appliance;

FIG. 2 is a perspective view showing an assembled butterfly needle/blood collection barrel with a vacuum blood sampling tube mounted therein in which the barrel is being held in place in the holding appliance of the invention, demonstrating how the invention is used in drawing blood while the phlebotomist holds the blood draw cannula or "butterfly needle" stationary after entering the patient's blood vessel;

FIG. 3 is a perspective view of the blood collection barrel and vacuum blood sampling tube used in FIGS. 1 and 2;

FIG. 4 is a perspective view of the assembled butterfly needle/blood and collection barrel of FIGS. 1 and 2, removed from the holding appliance;

FIG. 5 shows parts of one embodiment the appliance before assembly, with the larger band intended to go around the user's wrist with the smaller band in place across the larger band;

FIG. 6 is a perspective view of the appliance of the invention illustrating the use of hook and loop attachments in the wrist band and blood collection barrel holder of the appliance; and FIG. 7 is a perspective view of an alternate embodiment of the appliance of the present invention in which the blood collection barrel holder is a fixed elastic band.

DETAILED DESCRIPTION OF PREFERRED EMBODIMENTS OF THE INVENTION

The preferred appliance 10 of the invention is generally illustrated in FIGS. 1, 2, and 6, including a wristband 12, and a barrel holder 14. The appliance is shown as it would be used with a Vacutainer® vacuum blood drawing system 16 (available from Becton, Dickenson & Company), just prior to insertion of the barrel 18 of the system into the barrel holder 14 (FIG. 1). Of course, other types of collection systems could be used, solong as the container into which the blood is being drawn can be held in place on the wristband. It is preferred in such alternate embodiments that the collection system include a vacuum container as in the Vacutainer® vacuum blood drawing system. Wrist band 12 is shown in its closed position, as it would appear on the wrist of an operator (FIG. 2).

As best illustrated in FIG. 4, barrel 18 of the Vacutainer blood drawing system 16 has a nipple 20 at its distal end, and a length of flexible tubing 22 attached to the nipple. A shielded internal needle (not shown) extending proximally from nipple 20 is intended to penetrate a seal on the distal end of the vacuum blood sampling tube after the cannula 30 has been introduced into the patient's blood vessel, as described in more detail below. A "butterfly" blood drawing assembly 26 is attached to the distal end of the tubing 22. Butterfly assembly 26 includes a pair of laterally disposed flaps 28 and a blood draw or "indwelling" cannula 30 with a sharp point 32 at its distal end. Flaps 28 are made of a flexible material so that they can be pinched together by the operator to more easily manipulate the cannula as it is introduced into the patient's blood vessel. The pinched flaps, together with placement on the patient's hand, wrist, or arm of the operator's free fingers and heel of the hand on which appliance 10 is held, are used to steady the positioning of the indwelling cannula 30 while the blood sampling takes place. The Vacutainer/butterfly combination is so frequently used, the combination represents an industry standard as a method of drawing blood in children and adults who present with difficulty to the blood sampling process. The butterfly needle comes with a small gauge needle that affords the phlebotomist a greater control of penetration and canalization of the intended blood vessel.

A Vacutainer blood drawing assembly 40 is illustrated in FIG. 3. The assembly includes a rigid tube 42 (preferably made of glass or other clear rigid bio-compatible material) which is clear to enable the operator to see the blood gathering in the tube as the blood draw process proceeds. Tube 42 is closed off at its distal end by a resilient stopper or seal 44 to maintain a vacuum produced in the tube during its assembly. The operation of the Vacutainer assembly (which is well known in the health industry) entails placing container 40 in barrel 18 and pressing it home so that the shielded needle inside the barrel (not shown) penetrates seal 44, opening a clear channel between cannula 30 and the inner vacuum of the tube 42.

Turning now to FIGS. 5 and 6, one embodiment of the appliance 10 of the present invention is illustrated. As shown in these figures, wristband 12 includes complimentary hook and loop (Velcro®) attachment strips 46 and 48 which are affixed to opposite sides of the opposite ends 52 and 54 of the band. The length of the band is chosen to accommodate a range of typical operator wrist sizes. Thus, when the phlebotomist is preparing to draw blood, he or she places the wristband 12 on his or her wrist, and fixes it in place by drawing it snugly around the wrist and mating the complementary hook and loop strips 46 and 48.

The barrel holding band 14 is affixed to the outer surface 56 of wristband 12 so that the barrel holding band lies across the wristband and along the longitudinal axis A-A of the phlebotomist's arm as shown in FIG. 2. In the illustrated embodiment, the barrel holding band is affixed by a series of stitches 58, although it may be affixed in any other desired manner. The opposite ends of the barrel holding band have hook and loop strips 47 and 49 affixed on their reverse sides so that the band can be pulled tightly about barrel 18 and attached to hold it snugly in place.

Although the use of hook and loop strips (Velcro) has been illustrated in these figures, other attachment means could be used for either the wristband or the barrel holding band. Indeed, one or both of the bands could be made of a continuous elastic material so that the barrel is held in place under the tension provided by the elastic material. For example, an alternate design for holding barrel 18 is illustrated in FIG. 6 including an elastic band 60 affixed at either end to opposite edges 70 and 72 of the wristband. Here the elastic holding band 60 is of a length which ensures that the barrel is held firmly in place by the tension produced by elasticity of the band. Additionally, a bit of rubber of other high friction material 62 can be placed under the band to further resist dislodgment of the barrel, once it is in place.

Application

The appliance of the present invention may be used with a patient that has been referred to a phlebotomist for blood sampling which proceeds as discussed below. The phlebotomist seats (usually) the patient and selects a blood vessel from which to draw a blood sample.

Obtaining a routine blood sample occurs in two steps: 1) The vessel has to be penetrated successfully, and 2) the blood has to be extracted. The appliance of the present invention provides significant assistance with each of these two essential steps:

Step I

In the first step, the appliance of the present invention allows the phlebotomist to maintain the successful cannualization of the selected vessel in the following ways:

The appliance positions and maintains the barrel, in plain view on the phlebotomist's wrist. It also positions the barrel in the proper spatial orientation for easy insertion of the vacuum blood sampling tube. Finally, the appliance eliminates the need to leave the butterfly needle free and unattended while still in the patient's cannualized vessel in order to manipulate the vacuum blood sampling tube (s) and/or the barrel.

Step II

In the second step of the sampling process, the appliance of the invention allows the phlebotomist to successfully extract the blood sample. The phlebotomist is able to use both hands to continuously adjust the extraction patient (e.g., the patient's arm) and the "butterfly" needle to secure the even uninterrupted flow of blood sampling into the collection tube. Also, if it is necessary, in some instances, leave the butterfly needle to "dangle" in the patient's blood vessel while the vacuum blood sampling tube and barrel are engaged, the use of both hands during the procedure reduces the risk of over-penetration, laceration of the vascular wall, or premature extraction of the needle if the patient (child or adult) is combative or uncooperative. Also, the appliance facilitates the successive insertion of multiple vacuum sampling tubes. Finally, the blood filling rate and amounts are more easily visualized and monitored.

Thus, the blood drawing process can be completed in a significantly safer manner without the usual associated risks including asking the patient to assist by holding the barrel or the cannula in place.

While the present invention is described above in connection with preferred or illustrative embodiments, these embodiments are not intended to be exhaustive or limiting of the invention. Rather, the invention is intended to cover all alternative, modifications and equivalents included within its spirit and scope, as defined by the appended claims.

What I claim is:

1. An appliance fitted for facilitating the blood drawing process by a phlebotomist comprising:
   a flexible band for attachment across the wrist of the phlebotomist,
   a holder affixed and oriented generally perpendicularly to the longitudinal axis of the flexible band for receiving and holding a vacuum blood collection barrel during the blood drawing process; and
   a vacuum blood collection barrel, positioned in the holder generally parallel to the longitudinal axis of the band, for receiving blood sampling tubes.

2. The appliance of claim 1 in which the flexible band is made of an elastic fabric.

3. The appliance of claim 1 in which the flexible band has complimentary hook and loop attachment strips at its opposite ends to close the band about the wrist of the phlebotomist.

4. The appliance of claim 1 in which the band is sufficiently long to accommodate a range of wrist sizes.

5. The appliance of claim 1 in which the holder is a band including complimentary hook and loop attachments strips at either end.

6. The appliance of claim 1 in which the holder is an elastic band.

7. The appliance of claim 1 in which the blood collection barrel is in fluid communication with a butterfly blood drawing assembly.

8. The appliance of claim 1 in which the blood collection barrel has a nipple at its distal end and a length of flexible tubing attached to the nipple extending unobstructed from one end of the holder and being in fluid communication with a butterfly blood drawing assembly, the other end of the barrel being open and unobstructed by the holder to enable the barrel to receive the blood sampling tubes.

9. The appliance of claim 1 in which the blood collection container is generally cylindrical.

10. An appliance fitted for facilitating the blood drawing process by a phlebotomist comprising:
    a flexible band for attachment across the wrist of the phlebotomist,
    a holder oriented generally perpendicularly to the longitudinal axis of the band affixed to the band for receiving and holding a vacuum blood collection barrel with its opposite ends unobstructed during the blood drawing process; and
    a vacuum blood collection barrel positioned in the holder generally parallel to the longitudinal axis of the band for receiving blood sampling tubes.

11. The appliance of claim 10 in which the flexible band is made of an elastic fabric.

12. The appliance of claim 10 in which the band has complimentary hook and loop attachment strips at its opposite ends to close the band about the wrist.

13. The appliance of claim 10 in which the band is sufficiently long to accommodate a range of typical operator wrist sizes.

14. The appliance of claim 10 in which the blood collection container is generally cylindrical.

15. The appliance of claim 10 in which the holder is a band with complimentary hook and loop attachments trips at either end.

16. An appliance fitted for facilitating the blood drawing process by a phlebotomist comprising:
- a flexible band for attachment across the wrist of the phlebotomist,
- a holder affixed and oriented generally perpendicularly to the longitudinal axis of the band for receiving and holding a vacuum blood collection barrel during the blood drawing process;
- a vacuum blood collection barrel, positioned in the holder generally parallel to the longitudinal axis of the band, for receiving blood sampling tubes,
- the blood collection barrel having a nipple at its distal end and a length of flexible tubing attached to the nipple in fluid communication with a butterfly blood drawing assembly extending unobstructed from one end of the holder; and
- a blood sampling tube positioned in the barrel.

* * * * *